United States Patent
Shakhnovich

(10) Patent No.: US 7,674,905 B2
(45) Date of Patent: Mar. 9, 2010

(54) FLUOROQUINOLONOQUINOLONES AND INKJET INK COMPOSITIONS COMPRISING THE SAME

(75) Inventor: Alexander I. Shakhnovich, Westford, MA (US)

(73) Assignee: Cabot Corporation, Boston, MA (US)

( * ) Notice: Subject to any disclaimer, the term of this patent is extended or adjusted under 35 U.S.C. 154(b) by 276 days.

(21) Appl. No.: 11/388,732

(22) Filed: Mar. 24, 2006

(65) Prior Publication Data

US 2006/0217458 A1 Sep. 28, 2006

Related U.S. Application Data

(60) Provisional application No. 60/665,290, filed on Mar. 24, 2005, provisional application No. 60/763,547, filed on Jan. 31, 2006.

(51) Int. Cl.
*C08K 5/3437* (2006.01)
*C07D 221/18* (2006.01)

(52) U.S. Cl. .............................. 546/61; 524/89; 524/92; 524/102; 106/31.77; 106/498; 523/160

(58) Field of Classification Search ........................ None
See application file for complete search history.

(56) References Cited

U.S. PATENT DOCUMENTS

| | | | | |
|---|---|---|---|---|
| 3,334,102 | A * | 8/1967 | Aldridge et. al. | 546/70 |
| 4,142,890 | A * | 3/1979 | Bloom et al. | 430/37 |
| 4,946,509 | A | 8/1990 | Schwartz et al. | |
| 5,837,045 | A | 11/1998 | Johnson et al. | |
| 5,851,280 | A * | 12/1998 | Belmont et al. | 106/472 |
| 5,854,691 | A | 12/1998 | Lim et al. | |
| 5,922,118 | A | 7/1999 | Johnson et al. | |
| 6,040,789 | A | 3/2000 | Nishida et al. | |
| 6,472,471 | B2 * | 10/2002 | Cooke et al. | 525/165 |
| 6,494,943 | B1 | 12/2002 | Yu et al. | |
| 6,506,245 | B1 | 1/2003 | Kinney et al. | |
| 6,641,653 | B2 | 11/2003 | Yu | |
| 6,896,726 | B2 | 5/2005 | Bugnon et al. | |
| 6,936,097 | B2 | 8/2005 | Shakhnovich | |
| 6,942,724 | B2 | 9/2005 | Yu | |
| 7,223,302 | B2 | 5/2007 | Shakhnovich | |
| 7,307,170 | B2 * | 12/2007 | Kaul et al. | 546/38 |
| 2007/0277699 | A1 | 12/2007 | Bauer | |

FOREIGN PATENT DOCUMENTS

| | | |
|---|---|---|
| JP | 07-041689 | 2/1995 |
| JP | 10-017783 | 5/1998 |
| JP | 10-130554 | 5/1998 |
| JP | 11-080576 | 5/1998 |
| JP | 11-130972 | 5/1998 |
| JP | 2005041971 A * | 2/2005 |
| WO | WO 9748769 A1 * | 12/1997 |
| WO | WO 00/52102 | 9/2000 |
| WO | WO 01/30918 | 5/2001 |
| WO | WO 02/094944 | 11/2002 |

OTHER PUBLICATIONS

E.E. Jaffe; H. Matrick: "Synthesis of Epindolidione" Journal of Organic Chemistry, vol. 33, No. 11, Nov. 1968, pp. 4004-4010.
C.K. Kim; C. A. Maggiulli: "A New Synthesis of Dibenzo[b,g][1,5]naphthyridine-6,12(5H,11H)dione (Epindolidione)" Journal of Heterocyclic Chemistry, vol. 16, 1979, pp. 1651-1653.
International Search Report and Written Opinion for PCT/US2006/010564, mailed Jul. 17, 2007.
International Preliminary Report on Patentability for PCT/US2006/010564, mailed Oct. 4, 2007.
JP11-184157 to Toyo Ink Mfg. Co. Ltd. Publication Date Jul. 9, 1999 Abstract Only (from Patent Abstracts of Japan).
JP11-184158 to Toyo Ink Mfg. Co. Ltd. Publication Date Jul. 9, 1999 Abstract Only (from Patent Abstracts of Japan).
JP11-184159 to Toyo Ink Mfg. Co. Ltd. Publication Date Jul. 9, 1999 Abstract Only (from Patent Abstracts of Japan).
JP11-184160 to Toyo Ink Mfg. Co. Ltd. Publication Date Jul. 9, 1999 Abstract Only (from Patent Abstracts of Japan).
JP11-184161 to Toyo Ink Mfg. Co. Ltd. Publication Date Jul. 9, 1999 Abstract Only (from Patent Abstracts of Japan).
JP11-184162 to Toyo Ink Mfg. Co. Ltd. Publication Date Jul. 9, 1999 Abstract Only (from Patent Abstracts of Japan).

* cited by examiner

*Primary Examiner*—David Wu
*Assistant Examiner*—Vu Nguyen

(57) ABSTRACT

The present invention relates to modified yellow pigments comprising yellow pigments having attached at least one organic group. The yellow pigment is a fluoroquinolonoquinolone pigment. Also disclosed are inkjet ink compositions comprising these modified yellow pigments and inkjet ink sets comprising these inkjet ink compositions. Other applications are also disclosed.

13 Claims, No Drawings

FLUOROQUINOLONOQUINOLONES AND INKJET INK COMPOSITIONS COMPRISING THE SAME

CROSS-REFERENCE TO RELATED APPLICATIONS

This patent application claims the benefit of U.S. Provisional Patent Application Nos. 60/665,290, filed Mar. 24, 2005, and 60/763,547, filed Jan. 31, 2006.

BACKGROUND OF THE INVENTION

1. Field of the Invention

The present invention relates to modified yellow pigments comprising a yellow pigment having attached at least one organic group and inkjet ink compositions comprising them. The yellow pigment comprises at least one fluorine group.

2. Description of the Related Art

An inkjet ink composition generally consists of a vehicle, which functions as a carrier, and a colorant such as a dye or pigment. Additives and/or cosolvents can also be incorporated in order to adjust the inkjet ink to attain the desired overall performance properties.

Inkjet ink compositions comprising yellow pigment has been an area of particular focus for inkjet ink manufacturers. There has been a need in the industry for an inkjet ink composition comprising a yellow pigment having excellent lightfastness and the proper balance of color strength and hue, along with good overall dispersion stability. Various classes of yellow pigments have been prepared, each with varying degrees of lightfastness and color. For example, U.S. Pat. No. 3,334,102 describes the preparation of quinolonoquinolones, which are described as having good lightfastness. Various substituted quinolonoquinolones have also been prepared. For example, JP 11-130972 and 10-017783 describe the preparation of halogenated quinolonoquinolones.

In general, pigments alone, including yellow pigments, are not readily dispersible in liquid vehicles. A variety of techniques have been developed which can provide stable pigment dispersions that can be used in inkjet printing. For example, dispersants can be added to the pigment to improve its dispersibility in a particular medium. Examples of dispersants include water-soluble polymers and surfactants. Typically, these polymeric dispersants have a molecular weight less than 20,000 in order to maintain solubility and therefore pigment stability. Yellow pigment dispersions have also been prepared using this technique. For example, JP 10-130554 describes inkjet ink compositions comprising substituted quinolonoquinolones which further comprise a rosin, resin, surfactant, or dispersant.

The surface of pigments contain a variety of different functional groups, and the types of groups present depend on the specific class of pigment. Several methods have been developed for grafting materials and, in particular, polymers to the surface of these pigments. For example, it has been shown that polymers can be attached to carbon blacks containing surface groups such as phenols and carboxyl groups. However, methods which rely on the inherent functionality of a pigment's surface cannot be applied generally because not all pigments have the same specific functional groups.

Methods for the preparation of modified pigment products, including modified yellow pigments, have also been developed. These methods can be used to produce pigments with a variety of different attached functional groups. For example, U.S. Pat. No. 5,851,280 discloses methods for the attachment of organic groups onto pigments including, for example, attachment via a diazonium reaction wherein the organic group is part of the diazonium salt. Other methods to prepare modified pigments have also been described. For example, PCT Publication No. WO 01/51566 discloses methods of making a modified pigment by reacting a first chemical group and a second chemical group to form a pigment having attached a third chemical group. Ink compositions, including inkjet inks, containing these pigments are also described.

While these methods provide modified pigments, including modified yellow pigments, having attached groups, there remains a need in the industry for an inkjet ink composition comprising a yellow pigment having excellent lightfastness the proper balance of color strength, and/or hue along with good dispersion stability.

SUMMARY OF THE INVENTION

The present invention relates to a modified yellow pigment comprising a yellow pigment having attached at least one organic group. The yellow pigment has the structure:

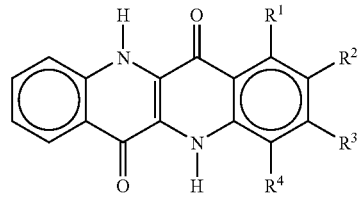

wherein one of $R^1$-$R^4$ is fluorine and three of $R^1$-$R^4$ are hydrogen. Various compositions comprising this modified yellow pigment are disclosed. For example, inkjet ink compositions comprising a liquid vehicle and this modified yellow pigment are described as well as an inkjet ink set comprising this inkjet ink composition.

The present invention relates to a modified yellow pigment comprising a yellow pigment having attached at least one organic group. The yellow pigment has the structure:

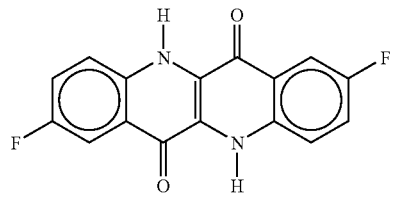

Various compositions comprising this modified yellow pigment are disclosed. For example, inkjet ink compositions comprising a liquid vehicle and this modified yellow pigment are described as well as an inkjet ink set comprising this inkjet ink composition.

The present invention further relates to a yellow pigment having the structure:

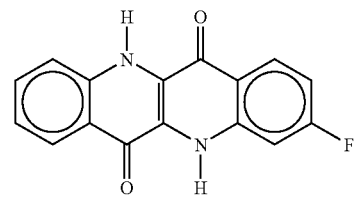

This pigment can be used to prepare a modified yellow pigment of the present invention and can also be used to prepare an inkjet ink composition and/or inkjet ink set of the present invention. In addition, various compositions comprising this yellow pigment are also disclosed.

It is to be understood that both the foregoing general description and the following detailed description are exemplary and explanatory only and are intended to provide further explanation of the present invention, as claimed.

Applicants specifically incorporate the entire contents of all references cited in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof and all integers and fractions within the range. It is not intended that the scope of the invention be limited to the specific values recited when defining a range.

DETAILED DESCRIPTION OF THE INVENTION

The present invention relates to modified yellow pigments and inkjet ink compositions comprising modified yellow pigments.

The modified yellow pigment of the present invention comprises a yellow pigment having attached at least one organic group. In one embodiment, the yellow pigment is a quinolonoquinolone pigment having the structure:

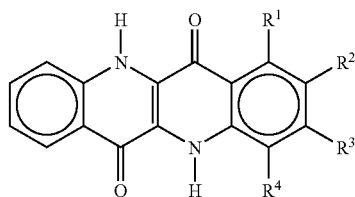

Each of $R^1$-$R^4$ is either a hydrogen or a fluorine group. In particular, three of these groups are hydrogen and one is fluorine. Thus, for this embodiment, the yellow pigment is a monofluoroquinolonoquinolone wherein one of $R^1$-$R^4$ is a fluorine group and the rest are hydrogen. Preferably, $R^2$ is a fluorine group, and each of $R^1$, $R^3$, and $R^4$ is a hydrogen. Also preferably $R^3$ is a fluorine group, with the remaining substituents being hydrogen.

In another embodiment, the yellow pigment of the modified yellow pigment of the present invention is a quinolonoquinolone pigment having the structure:

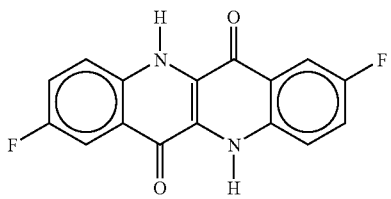

For this embodiment, the yellow pigment is a difluoroquinolonoquinolone pigment in which each of the aromatic rings of the quinolonoquinolone structure comprises one fluorine group in a position para to the nitrogen groups. The remaining substituents are hydrogen.

The yellow pigment can have a wide range of BET surface areas, as measured by nitrogen adsorption, depending on the desired properties of the yellow pigment. As is known to those skilled in the art, a higher surface area will correspond to a smaller particle size. If a higher surface area is not readily available for the desired application, it is also well recognized by those skilled in the art that the pigment may be subjected to conventional size reduction or comminution techniques, such as ball or jet milling, to reduce the pigment to a smaller particle size, if desired.

As described above, the modified yellow pigment of the present invention comprises a yellow pigment having attached at least one organic group, such as an alkyl group or an aromatic. Preferably, the organic group comprises at least one ionic group, at least one ionizable group, or a mixture thereof. An ionic group is either anionic or cationic and is associated with a counterion of the opposite charge including inorganic or organic counterions such as $Na^+$, $K^+$, $Li^+$, $NH_4^+$, $NR'_4^+$, acetate, $NO_3^-$, $SO_4^{-2}$, $R'SO_3^-$, $R'OSO_3^-$, $OH^-$, and $Cl^-$, where R' represents hydrogen or an organic group such as a substituted or unsubstituted aryl and/or alkyl group. An ionizable group is one that is capable of forming an ionic group in the medium of use. Anionizable groups form anions and cationizable groups form cations. Preferably, the attached group is an organic group. Organic ionic groups include those described in U.S. Pat. No. 5,698,016, the description of which is fully incorporated herein by reference.

Anionic groups are negatively charged ionic groups that may be generated from groups having ionizable substituents that can form anions (anionizable groups), such as acidic substituents. They may also be the anion in the salts of ionizable substituents. Representative examples of anionic groups include $-COO^-$, $-SO_3-$, $-OSO_3^-$, $-HPO_3^-$, $-OPO_3^{-2}$, and $-PO_3^{-2}$. Representative examples of anionizable groups include $-COOH$, $-SO_3H$, $-PO_3H_2$, $-R'SH$, $-R'OH$, and $-SO_2NHCOR'$, where R' represents hydrogen or an organic group such as a substituted or unsubstituted aryl and/or alkyl group. Preferably, the attached group comprises a carboxylic acid group, a sulfonic acid group, a sulfate group, a phosphonate group, or salts thereof. For example, the attached group may be an organic group such as a benzene carboxylic acid group, a benzene dicarboxylic acid group, a benzene tricarboxylic acid group, a benzene sulfonic acid group, or salts thereof. The attached organic group may also be a substituted derivative of any of these.

Cationic groups are positively charged organic ionic groups that may be generated from ionizable substituents that can form cations (cationizable groups), such as protonated amines. For example, alkyl or aryl amines may be protonated in acidic media to form ammonium groups $-NR'_2H^+$, where R' represent an organic group such as a substituted or unsubstituted aryl and/or alkyl group. Cationic groups may also be positively charged organic ionic groups. Examples include quaternary ammonium groups ($-NR'_3^+$) and quaternary phosphonium groups ($-PR'_3^+$). Here, R', which can be the same or different, represents hydrogen or an organic group such as a substituted or unsubstituted aryl and/or alkyl group. Preferably, the attached group comprises an alkyl amine group or a salt thereof or an alkyl ammonium group.

The organic group may also be a polymeric group. Preferably, the polymeric group comprises the ionic or ionizable groups described above. Thus, the organic group may be a polymeric group comprising one or more anionic or anionizable groups. Examples include, but are not limited to, polyacids such as polyacrylic acid, polymethacrylic acid, copolymers of acrylic acid or methacrylic acid, including styrene-acrylic acid polymers, and hydrolyzed derivatives of maleic anhydride-containing polymers. The organic group may also be a polymeric group comprising one or more cationic or cationizable groups. Examples include, but are not limited to, linear or branched polyamines such as polyethyleneimine (PEI), oligomers of ethyleneimine (such as pentaethyleneamine, PEA) and derivatives of polyethyleneimine. The organic group may also be a polymeric group comprising one or more naturally occurring polymers, such as proteins or carbohydrates.

The modified yellow pigment may be prepared using methods known to those skilled in the art such that organic chemical groups are attached to the pigment. This provides a more stable attachment of the groups onto the pigment compared to adsorbed groups, e.g., polymers, surfactants, and the like. For example, the modified pigments can be prepared using the methods described in U.S. Pat. Nos. 5,554,739, 5,707,432, 5,837,045, 5,851,280, 5,885,335, 5,895,522, 5,900,029, 5,922,118, and 6,042,643, and PCT Publication WO 99/23174, the descriptions of which are fully incorporated herein by reference. Such methods provide for a more stable attachment of the groups onto the pigment compared to dispersant type methods, which use, for example, polymers and/or surfactants.

The present invention further relates to monofluoroquinolonoquinolone pigments. Preferably, the pigment has the structure shown above wherein one of $R^1$-$R^4$ is fluorine and three are hydrogen. For example, either $R^2$ or $R^3$ may be a fluorine group, with the remaining substituents being hydrogen. Most preferred is the monofluoroquinolonoquinolone yellow pigment having the structure:

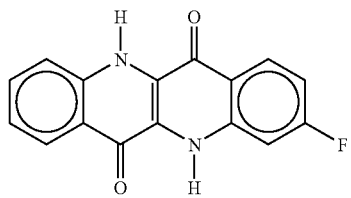

This yellow pigment has been surprisingly found to have desirable overall color properties, especially in comparison to other monohaloquinolonoquinolones. In addition, the yellow pigment may be used to prepare a modified yellow pigment of the present invention.

Both the modified yellow pigments as well as the yellow pigments of the present invention may be used in a variety of different applications, including, for example, plastic compositions, aqueous or non-aqueous inks, aqueous or non-aqueous coatings, rubber compositions, paper compositions and textile compositions. In particular, these pigments may be used in aqueous compositions, including, for example, automotive and industrial coatings, paints, toners, adhesives, latexes, and inks. The pigments have been found to be most useful in ink composition, especially inkjet inks.

Thus, the present invention further relates to an inkjet ink composition comprising a vehicle and a modified yellow pigment. The vehicle can be either an aqueous or non-aqueous liquid vehicle, but is preferably a vehicle that contains water. Thus, the vehicle is preferably an aqueous vehicle, which is a vehicle that contains greater than 50% water and can be, for example, water or mixtures of water with water miscible solvents such as alcohols. Non-aqueous vehicles are those that contain less than 50% water or are not miscible with water. Preferably the aqueous vehicle is water, and the inkjet ink composition is an aqueous inkjet ink composition.

The modified yellow pigment can be any of the modified pigments described above and can be present in the inkjet ink composition in an amount effective to provide the desired image quality (for example, optical density) without detrimentally affecting the performance of the inkjet ink. For example, typically, the modified yellow pigment can be present in an amount as low as about 0.1% by weight, preferably 0.5% by weight, and as high as about 30% by weight, preferably 25% by weight based on the weight of the ink. More or less modified pigment may be used depending on the amount of attached organic group, particularly when the organic group is a polymeric group. For example, higher levels of modified pigments having attached polymeric groups, by weight, may be used than for conventional pigments due to the presence of the attached groups. It is also within the bounds of the present invention to use a mixture of the modified yellow pigment described herein and unmodified pigments, other modified pigments (such as other pigments having attached organic groups described above), or both.

The inkjet ink composition of the present invention can be formed with a minimum of additional components (additives and/or cosolvents) and processing steps. However, suitable additives may be incorporated in order to impart a number of desired properties while maintaining the stability of the compositions. For example, surfactants and/or dispersants, humectants, drying accelerators, penetrants, biocides, binders, and pH control agents, as well as other additives known in the art, may be added. The amount of a particular additive will vary depending on a variety of factors but generally ranges between 0% and 40%.

Dispersing agents (surfactants and/or dispersants) may be added to further enhance the colloidal stability of the composition or to change the interaction of the ink with either the printing substrate, such as printing paper, or with the ink printhead. Various anionic, cationic and nonionic dispersing agents can be used in conjunction with the ink composition of the present invention, and these may be in solid form or as a water solution.

Representative examples of anionic dispersants or surfactants include, but are not limited to, higher fatty acid salts, higher alkyldicarboxylates, sulfuric acid ester salts of higher alcohols, higher alkyl-sulfonates, alkylbenzenesulfonates, alkylnaphthalene sulfonates, naphthalene sulfonates (Na, K, Li, Ca, etc.), formalin polycondensates, condensates between higher fatty acids and amino acids, dialkylsulfosuccinic acid ester salts, alkylsulfosuccinates, naphthenates, alkylether carboxylates, acylated peptides, α-olefin sulfonates, N-acrylmethyl taurine, alkylether sulfonates, secondary higher alcohol ethoxysulfates, polyoxyethylene alkylphenylether sulfates, monoglycylsulfates, alkylether phosphates and alkyl phosphates. For example, polymers and copolymers of styrene sulfonate salts, unsubstituted and substituted naphthalene sulfonate salts (e.g. alkyl or alkoxy substituted naphthalene derivatives), aldehyde derivatives (such as unsubstituted alkyl aldehyde derivatives including formaldehyde, acetaldehyde, propylaldehyde, and the like), maleic acid salts, and mixtures thereof may be used as the anionic dispersing aids. Salts include, for example, $Na^+$, $Li^+$, $K^+$, $Cs^+$, $Rb^+$, and substituted and unsubstituted ammonium cations. Specific examples include, but are not limited to, commercial products such as Versa® 4, Versa® 7, and Versa® 77 (National Starch and Chemical Co.); Lomar® D (Diamond Shamrock Chemicals Co.); Daxad®19 and Daxad® K (W. R. Grace Co.); and Tamol® SN (Rohm & Haas). Representative examples of cationic surfactants include aliphatic amines, quaternary ammonium salts, sulfonium salts, phosphonium salts and the like.

Representative examples of nonionic dispersants or surfactants that can be used in ink jet inks of the present invention include fluorine derivatives, silicone derivatives, acrylic acid copolymers, polyoxyethylene alkyl ether, polyoxyethylene alkylphenyl ether, polyoxyethylene secondary alcohol ether, polyoxyethylene styrol ether, polyoxyethylene lanolin derivatives, ethylene oxide derivatives of alkylphenol formalin condensates, polyoxyethylene polyoxypropylene block polymers, fatty acid esters of polyoxyethylene polyoxypropylene alkylether polyoxyethylene compounds, ethylene glycol fatty acid esters of polyethylene oxide condensation type, fatty acid monoglycerides, fatty acid esters of polyglycerol, fatty acid esters of propylene glycol, cane sugar fatty acid esters, fatty acid alkanol amides, polyoxyethylene fatty acid amides and polyoxyethylene alkylamine oxides. For example, ethoxylated monoalkyl or dialkyl phenols may be used, such as Igepal® CA and CO series materials (Rhone-Poulenc Co.) Briji® Series materials (ICI Americas, Inc.), and Triton® series materials (Union Carbide Company). These nonionic surfactants or dispersants can be used alone or in combination with the aforementioned anionic and cationic dispersants.

The dispersing agents may also be a natural polymer or a synthetic polymer dispersant. Specific examples of natural polymer dispersants include proteins such as glue, gelatin, casein and albumin; natural rubbers such as gum arabic and tragacanth gum; glucosides such as saponin; alginic acid, and alginic acid derivatives such as propyleneglycol alginate, triethanolamine alginate, and ammonium alginate; and cellulose derivatives such as methyl cellulose, carboxymethyl cellulose, hydroxyethyl cellulose and ethylhydroxy cellulose. Specific examples of polymeric dispersants, including synthetic polymeric dispersants, include polyvinyl alcohols; polyvinylpyrrolidones; acrylic or methacrylic resins (often written as "(meth)acrylic") such as poly(meth)acrylic acid, acrylic acid-(meth)acrylonitrile copolymers, potassium (meth)acrylate-(meth)acrylonitrile copolymers, vinyl acetate-(metha)acrylate ester copolymers and (meth)acrylic acid-(meth)acrylate ester copolymers; styrene-acrylic or methacrylic resins such as styrene-(meth)acrylic acid copolymers, styrene-(meth)acrylic acid-(meth)acrylate ester copolymers, styrene-α-methylstyrene-(meth)acrylic acid copolymers, styrene-α-methylstyrene-(meth)acrylic acid-(meth)acrylate ester copolymers; styrene-maleic acid copolymers; styrene-maleic anhydride copolymers, vinyl naphthalene-acrylic or methacrylic acid copolymers; vinyl naphthalene-maleic acid copolymers; and vinyl acetate copolymers such as vinyl acetate-ethylene copolymer, vinyl acetate-fatty acid vinyl ethylene copolymers, vinyl acetate-maleate ester copolymers, vinyl acetate-crotonic acid copolymer and vinyl acetate-acrylic acid copolymer; and salts thereof.

Humectants and water soluble organic compounds may also be added to the inkjet ink composition of the present invention, particularly for the purpose of preventing clogging of the nozzle as well as for providing paper penetration (penetrants), improved drying (drying accelerators), and anti-cockling properties. Specific examples of humectants and other water soluble compounds that may be used include low molecular-weight glycols such as ethylene glycol, diethylene glycol, triethylene glycol, tetraethylene glycol and dipropylene glycol; diols containing from about 2 to about 40 carbon atoms, such as 1,3-pentanediol, 1,4-butanediol, 1,5-pentanediol, 1,4-pentanediol, 1,6-hexanediol, 1,5-hexanediol, 2,6-hexanediol, neopentylglycol (2,2-dimethyl-1,3-propanediol, 1,3-propanediol, 1,4-butanediol, 1,5-pentanediol, 1,6-hexanediol, 1,2,6-hexanetriol, poly(ethylene-co-propylene)glycol, and the like, as well as their reaction products with alkylene oxides, including ethylene oxides, including ethylene oxide and propylene oxide; triol derivatives containing from about 3 to about 40 carbon atoms, including glycerine, trimethylpropane, 1,3,5-pentanetriol, 1,2,6-hexanetriol, and the like as well as their reaction products with alkylene oxides, including ethylene oxide, propylene oxide, and mixtures thereof; neopentylglycol, (2,2-dimethyl-1,3-propanediol), and the like, as well as their reaction products with alkylene oxides, including ethylene oxide and propylene oxide in any desirable molar ratio to form materials with a wide range of molecular weights; thiodiglycol; pentaerythritol and lower alcohols such as ethanol, propanol, iso-propyl alcohol, n-butyl alcohol, sec-butyl alcohol, and tert-butyl alcohol, 2-propyn-1-ol (propargyl alcohol), 2-buten-1-ol, 3-buten-2-ol, 3-butyn-2-ol, and cylcopropanol; amides such as dimethyl formaldehyde and dimethyl acetamide; ketones or ketoalcohols such as acetone and diacetone alcohol; ethers such as tetrahydrofurane and dioxane; cellosolves such as ethylene glycol monomethyl ether and ethylene glycol monoethyl ether, triethylene glycol monomethyl (or monoethyl) ether; carbitols such as diethylene glycol monomethyl ether, diethylene glycol monoethyl ether, and diethylene glycol monobutyl ether; lactams such as 2-pyrrolidone, N-methyl-2-pyrrolidone and ε-caprolactam; urea and urea derivatives; inner salts such as betaine, and the like; thio (sulfur) derivatives of the aforementioned materials including 1-butanethiol; t-butanethiol 1-methyl-1-propanethiol, 2-methyl-1-propanethiol; 2-methyl-2-propanethiol; thiocyclopropanol, thioethyleneglycol, thiodiethyleneglycol, trithio- or dithio-diethyleneglycol, and the like; hydroxyamide derivatives, including acetylethanolamine, acetylpropanolamine, propylcarboxyethanolamine, propylcarboxy propanolamine, and the like; reaction products of the aforementioned materials with alkylene oxides; and mixtures thereof. Additional examples include saccharides such as maltitol, sorbitol, gluconolactone and maltose; polyhydric alcohols such as trimethylol propane and trimethylol ethane; N-methyl-2-pyrrolidene; 1,3-dimethyl-2-imidazolidinone; sulfoxide derivatives containing from about 2 to about 40 carbon atoms, including dialkylsulfides (symmetric and asymmetric sulfoxides) such as dimethylsulfoxide, methylethylsulfoxide, alkylphenyl sulfoxides, and the like; and sulfone derivatives (symmetric and asymmetric sulfones) containing from about 2 to about 40 carbon atoms, such as dimethylsulfone, methylethylsulfone, sulfolane (tetramethylenesulfone, a cyclic sulfone), dialkyl sulfones, alkyl phenyl sulfones, dimethylsulfone, methylethylsulfone, diethylsulfone, ethylpropylsulfone, methylphenylsulfone, methylsulfolane, dimethylsulfolane, and the like. Such materials may be used alone or in combination.

Biocides and/or fungicides may also be added to the inkjet ink composition of the present invention. Biocides are important in preventing bacterial growth since bacteria are often larger than ink nozzles and can cause clogging as well as other printing problems. Examples of useful biocides include, but are not limited to, benzoate or sorbate salts, and isothiazolinones.

Various polymeric binders can also be used in conjunction with the inkjet ink composition of the present invention to adjust the viscosity of the composition as well as to provide other desirable properties. Suitable polymeric binders include, but are not limited to, water soluble polymers and copolymers such as gum arabic, polyacrylate salts, polymethacrylate salts, polyvinyl alcohols, hydroxypropylenecellulose, hydroxyethylcellulose, polyvinylpyrrolidinone, polyvinylether, starch, polysaccharides, polyethyleneimines with or without being derivatized with ethylene oxide and propylene oxide including the Discole® series (DKS International); the Jeffamine® series (Texaco); and the like. Additional examples of water-soluble polymer compounds include various dispersants or surfactants described above, including, for example, styrene-acrylic acid copolymers, styrene-acrylic acid-alkyl acrylate terpolymers, styrene-methacrylic acid copolymers, styrene-maleic acid copolymers, styrene-maleic acid-alkyl acrylate terpolymers, styrene-methacrylic acid-alkyl acrylate terpolymers, styrene-maleic acid half ester copolymers, vinyl naphthalene-acrylic acid copolymers, alginic acid, polyacrylic acids or their salts and their derivatives. In addition, the binder may be added or present in dispersion or latex form. For example, the polymeric binder may be a latex of acrylate or methacrylate copolymers or may be a water dispersible polyurethane.

Various additives for controlling or regulating the pH of the inkjet ink composition of the present invention may also be used. Examples of suitable pH regulators include various amines such as diethanolamine and triethanolamine as well as various hydroxide reagents. An hydroxide reagent is any reagent that comprises an OH⁻ ion, such as a salt having an hydroxide counterion. Examples include sodium hydroxide, potassium hydroxide, lithium hydroxide, ammonium hydroxide, and tetramethyl ammonium hydroxide. Other hydroxide salts, as well as mixtures of hydroxide reagents, can also be used. Furthermore, other alkaline reagents may also be used which generate OH⁻ ions in an aqueous medium. Examples include carbonates such as sodium carbonate, bicarbonates such as sodium bicarbonate, and alkoxides such as sodium methoxide and sodium ethoxide. Buffers may also be added.

Additionally, the inkjet ink composition of the present invention may further incorporate dyes to modify color balance and adjust optical density. Such dyes include food dyes, FD&C dyes, acid dyes, direct dyes, reactive dyes, derivatives of phthalocyanine sulfonic acids, including copper phthalocyanine derivatives, sodium salts, ammonium salts, potassium salts, lithium salts, and the like.

The inkjet ink composition can be purified and/or classified using any method known in the art. An optional counterion exchange step can also be used. In this way, unwanted impurities or undesirable large particles can be removed to produce an ink with good overall properties.

While modified yellow pigments are known in the art, surprisingly it has been found that modified yellow pigments comprising the mono- and difluoroquinolonoquinolone yellow pigment described above having attached at least one organic group can be prepared and used to prepare inkjet ink compositions having good overall properties, including good color and hue, excellent lightfastness, and good dispersion stability. Modified yellow pigments comprising other halogenated yellow pigments, particularly other haloquinolonoquinolones, did not result in inkjet ink compositions having these same properties.

The present invention further relates to an inkjet ink set which comprises various inkjet ink compositions and includes the inkjet ink composition of the present invention. The inkjet ink compositions of this set may differ in any way known in the art. For example, the inkjet ink set may comprise inkjet ink compositions comprising different types and/or colors of pigments, including, for example, an inkjet ink composition comprising a cyan pigment, an inkjet ink composition comprising a magenta pigment, and/or an inkjet ink composition comprising a black pigment. Other types of inkjet ink compositions may also be used, including, for example, compositions comprising agents designed to fix the inkjet ink compositions onto the substrate. Other combinations will be known in the art.

The present invention will be further clarified by the following examples which are intended to be only exemplary in nature.

EXAMPLES

Example 1 and Comparative Examples 1-3

Preparation of Symmetrically Substituted Quinolonoquinolone Pigments

The following general procedure was used to prepare symmetrically substituted quinonolonoquinolones, including bisfluoroquinolonoquinolones of the present invention, according to the three step reaction sequence shown in Scheme 1 below. In Scheme 1, for meta-substituted anilines such as those of Comparative Examples 2 and 3 in which multiple cyclization products may be formed, it is presumed that the cyclization predominantly forms the less hindered regio-isomeric product, and only this product is shown (Compound II).

Scheme 1

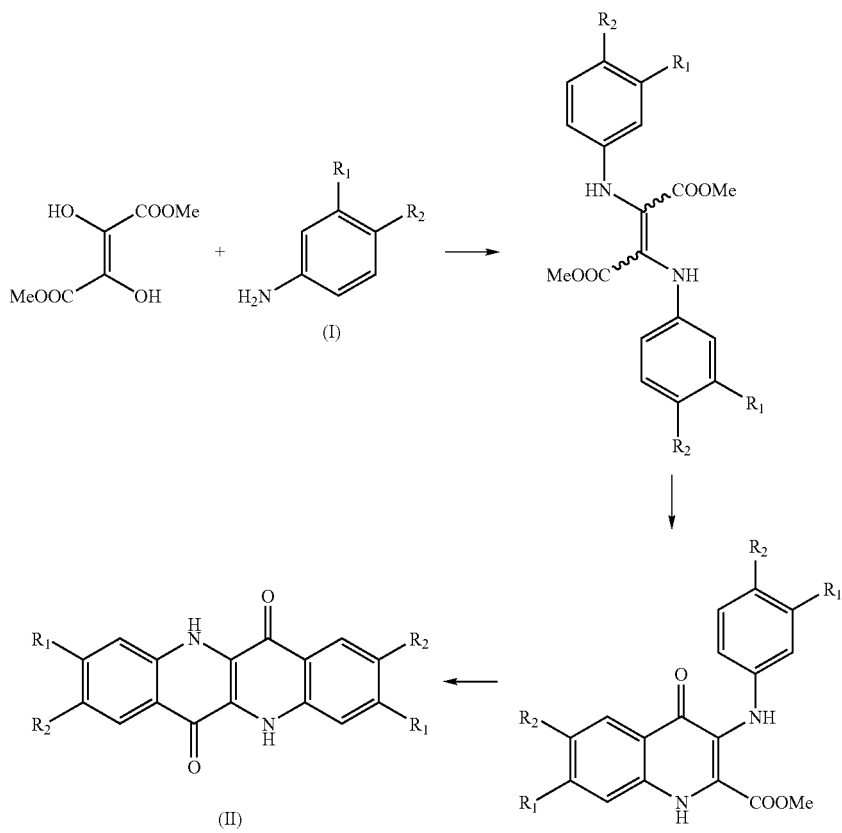

The specific starting substituted aniline (Compound I in Scheme 1) for each example is shown in Table 1 below.

TABLE 1

| Example No. | Substituted Aniline | $R^1$ | $R^2$ |
| --- | --- | --- | --- |
| Example 1 | 4-Fluoroaniline | H | F |
| Comp. Ex. 1 | 3-Fluoroaniline | F | H |
| Comp. Ex. 2 | 4-Chloroaniline | H | Cl |
| Comp. Ex. 3 | 3-Chloroaniline | Cl | H |

Step 1—Enamine Formation. In a round-bottom flask was added 142 mmol of dimethyl dihydroxyfumarate (prepared according to the procedure described in U.S. Pat. No. 3,334, 102), 80-90 ml of methyl alcohol, and 312.5 mmol of a substituted aniline shown in Table 1. To this mixture, while stirring with a teflon stir bar, was added 0.5 mL of concentrated HCl. A reflux condenser was attached to the flask, and the reaction mixture was heated at refluxed for six hours. The resulting reaction mixture was cooled to room temperature and left overnight in a refrigerator. In the morning, a thick paste was observed which was then filtered using a coarse fritted filter, washed with 50% (v:v) methanol-water mixture, and dried in a vacuum oven. The resulting 2,3-bis-(anilino)-but-2-enedioic acid dimethyl ester was obtained in yields ranging between 65-75%. According to NMR data, all were mixtures of E/Z isomers. These materials were used as is for the cyclization steps.

Step 2—First Cyclization. To a 3 liter round-bottom flask equipped with a magnetic stirrer, heated jacketed addition funnel, and a short downward condenser to distill of volatile products was added 100 mL of Dowtherm A (a euthectic mixture of 73.5% of phenyl ether and 26.5% biphenyl available from Dow). This was heated to reflux (255-265° C.). Separately, 100 g of the 2,3-bis-(anilino)-but-2-enedioic acid dimethyl ester prepared as described above was dissolved in 1000 ml of Dowtherm A which had been warmed to a temperature of approximately 120° C. The hot solution was then added gradually to the 3 liter flask from the heated addition funnel over 20-30 min. Reflux was maintained throughout the addition. Some Dowtherm A containing the ethanol by-product distilled off during the reaction. At the end of the addition, the reaction mixture was refluxed for an additional 15 minutes and then allowed to cool to room temperature, during which time the mono-cyclization product was observed crystallizing out. The slurry was allowed to sit overnight at room temperature, and the product was isolated by filtration using a coarse glass fritted filter carefully to avoid cracks in the precipitate cake. The precipitate was washed with petroleum ether until the filtrate appeared almost colorless with no perceptible odor of Dowtherm A. The precipitate was left under vacuum overnight. The resulting quinolone derivative (mono-cyclization product) was isolated in yields of approximately 75% and used as is in the second cyclization step.

Step 2—Second Cyclization. In a 750 ml 5-neck sulfuration flask, equipped with anchor stirrer, thermocouple, and Drierite tube was added 500 g of polyphosphoric acid. This was heated to 110° C. To this was added 60 g of the quinolone derivative described above with stirring. The addition took place over 10-15 minutes so that the material being added would be wetted with polyphosphoric acid evenly. After all of the material was added, the temperature was raised to 150° C., and the mixture was stirred at this temperature for 3 hours. The reaction mixture was allowed to cool to 80-90° C., and the resulting viscous mixture was poured into 2.5 liters of cold tap water. Hydrolysis of red polyphosphoric acid complex of the desired quinolonoquinolone product occurred quickly as the formation of a bright yellow precipitate of pigment was immediately observed. The precipitate was isolated by filtration using #2 filter paper and washed with copious amounts of DI water until the pH of the filtrate was between 5 and 6. The resulting wet presscake of quinolonoquinolone pigment was used as for producing modified pigments of the present invention. Yield of the yellow pigment was typically approximately 100% (on solid base).

Symmetrically substituted quinolonoquinolone pigments obtained by this process (Compound II in Scheme 1) are shown in Table 2 below, along with the observed color of each pigment.

TABLE 2

| Example No. | $R^1$ | $R^2$ | Observed Color |
| --- | --- | --- | --- |
| Example 1 | H | F | Greenish Yellow |
| Comp. Ex. 1 | F | H | Greenish Yellow |
| Comp. Ex. 2 | H | Cl | Reddish Yellow |
| Comp. Ex. 3 | Cl | H | Greenish Yellow |

Examples 2-3 and Comparative Examples 4-7

Preparation of Asymmetrically Substituted Quinolonoquinolone Pigments

The following general procedure was used to prepare asymmetrically substituted quinonolonoquinolones, including the mono-fluoroquinolonoquinolone of the present invention, according to the reaction sequence shown in Scheme 2 below. In Scheme 2, for meta-substituted anilines such as those of Example 2 and Comparative Examples 4-7 in which multiple cyclization products may be formed, it is presumed that the cyclization predominantly forms the less hindered regio-isomeric product, and only this product is shown (Compound III).

Scheme 2

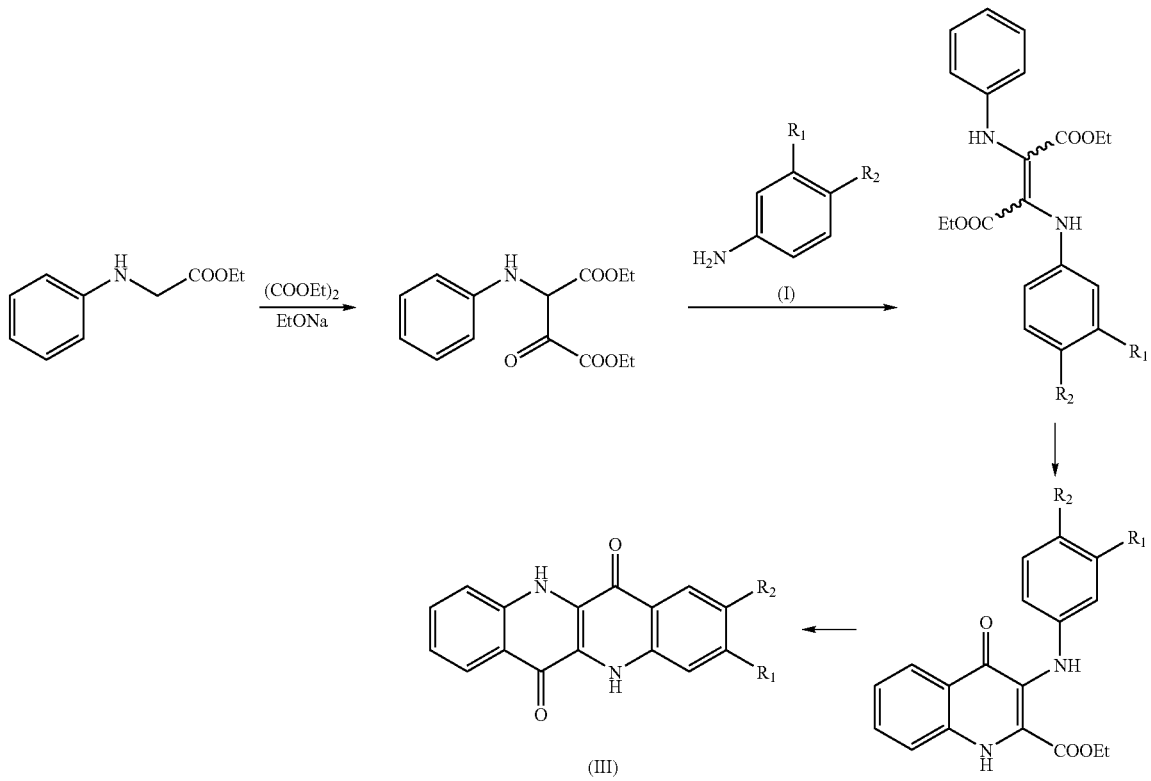

The specific starting substituted aniline (Compound I in Scheme 2) for each example is shown in Table 3 below.

TABLE 3

| Example No. | Substituted Aniline | $R^1$ | $R^2$ |
| --- | --- | --- | --- |
| Example 2 | 3-Fluoroaniline | F | H |
| Example 3 | 4-Fluoroaniline | H | F |
| Comp. Ex. 4 | 3-Chloroaniline | Cl | H |
| Comp. Ex. 5 | 3,4-Dichloroaniline | Cl | Cl |
| Comp. Ex. 6 | 3-Fluoro-4-toluidine | F | Me |
| Comp. Ex. 7 | 3-Chloro-4-toluidine | Cl | Me |

Step 1—Oxalacetate Condensation and Enamine Formation. To a 1 liter round-bottom flask equipped with a condenser with a moisture protection tube was added 42.8 g (0.63 mol) of solid sodium ethoxide and 290 ml of absolute ethyl alcohol. This was stirred with a magnetic stir bar for 15-20 min until most of the sodium ethoxide dissolved. To this was added 81.6 g (0.56 mol) of diethyl oxalate and 100 g (0.56 mol) of N-phenylglycine ethyl ester. The mixture was stirred at room temperature for 20-22 hours. To the resulting product was carefully added 54 mL of concentrated hydrochloric acid (38% HCl; d=1.18; 0.66 mol HCl) followed by 0.5 mol a substituted aniline shown in Table 3. The reaction mixture was heated at reflux for 6 hours. On cooling to room temperature, the desired 2-anilino-3-(substituted anilino)-but-2-ene-dioic acid diethyl ester crystallized out. This was isolated by filtration using a 600 mL funnel, pressed, and washed with 50% ethanol. The product was dried in a vacuum oven at 40° C. overnight to give approximately 110-120 g of the desired product, which was 60-75% yield. Although the material contained sodium chloride as a reaction by-product, this was used without further purification in the cyclization step. According to NMR data, all were mixtures of E/Z isomers.

Step 2—Cyclizations. Asymmetrically substituted quinolonquinolone pigments were obtained using the first cyclization and second cyclization steps described in Example 1 and Comparative Examples 1-3 above. The resulting products (Compound III in Scheme 2) are shown in Table 4 below, along with the observed color of each pigment.

TABLE 4

| Example No. | $R^1$ | $R^2$ | Observed Color |
| --- | --- | --- | --- |
| Example 2 | F | H | Yellow |
| Example 3 | H | F | Yellow |
| Comp. Ex. 4 | Cl | H | Yellow |
| Comp. Ex. 5 | Cl | Cl | Reddish Yellow |
| Comp. Ex. 6 | F | Me | Yellow |
| Comp. Ex. 7 | Cl | Me | Reddish Yellow |

Examples 4-6 and Comparative Examples 8-14

Preparation of Modified Yellow Pigments

The following general procedure was used to prepare modified yellow pigments comprising a yellow pigment having attached at least one organic group using the yellow pigments of Examples 1-3 and Comparative Examples 1-7.

A rotor-stator high shear mixer (Silverson L4RT-A) was fitted with a 2 liter stainless steel beaker mounted on a hot plate. Approximately 55 g of a yellow pigment presscake shown in Table 5 was added to the beaker along with 13.32 g of sulfanilic acid (242 mmol) followed by 1 liter of DI water. The mixture was homogenized for 15 min at 7,200 rpm while heating to 65-70° C. When the mixture reached this temperature, a solution of 16.9 g (245 mmol) of sodium nitrite in 100 mL water was added dropwise over 20 minutes. The reaction mixture was then stirred at 7,200 rpm for 90 minutes at 65-70° C. After this time, the mixture was allowed to cool to room temperature.

The properties of the resulting products are shown in Table 5 below.

TABLE 5

| Example No. | Pigment | $R^1$ | $R^2$ | Observations |
| --- | --- | --- | --- | --- |
| Example 4 | Example 1 | H | F | stable dispersion |
| Comp. Ex. 8 | Comp Ex. 1 | F | H | no stable dispersion |
| Comp. Ex. 9 | Comp. Ex. 2 | H | Cl | no stable dispersion |
| Comp. Ex. 10 | Comp. Ex. 3 | Cl | H | no stable dispersion |
| Example 5 | Example 2 | F | H | stable dispersion |

TABLE 5-continued

| Example No. | Pigment | $R^1$ | $R^2$ | Observations |
| --- | --- | --- | --- | --- |
| Example 6 | Example 3 | H | F | stable dispserion |
| Comp. Ex. 11 | Comp. Ex. 4 | Cl | H | no stable dispersion |
| Comp. Ex. 12 | Comp. Ex. 5 | Cl | Cl | no stable dispersion |
| Comp. Ex. 13 | Comp. Ex. 6 | F | Me | no stable dispersion |
| Comp. Ex. 14 | Comp. Ex. 7 | Cl | Me | no stable dispersion |

In Table 5, Example 4 and Comparative Examples 8-10 relate to modified pigments comprising symmetrically substituted quinolonoquinolones (Compound II of Scheme 1 above) while Examples 5-6 and Comparative Examples 11-14 relate to modified pigments comprising asymmetric derivatives (Compound III of Scheme 2 above). The results in Table 5 show that a modified yellow pigment comprising a yellow quinolononquinolone pigment having fluorine groups in positions para to the nitrogens and having attached benzene sulfonic acid salt groups formed stable aqueous pigment dispersions. By comparison, modified pigments comprising a yellow pigment having fluorine groups in different positions (Comparative Example 8) or modified pigments comprising a yellow pigment having chlorine groups in the same or different positions (Comparative Examples 9 and 10) did not form stable aqueous dispersions. The results also show that modified yellow pigments comprising a mono-fluoroquinolonoquinolone having attached benzenesulfonic acid groups (Examples 5 and 6) produced stable aqueous pigment dispersions whereas, for modified pigments comprising either mono-chloroquinolonoquinolone pigments (Comparative Example 11) or pigments in which one of the substituents of the quinolonoquinolone pigment is neither H nor a fluorine group (Comparative Examples 12-14), no stable pigment dispersion resulted.

The modified pigment dispersion of Examples 4-6 were found to have a mean particle size of 350-500 nm (measured using a Microtrac UPA 150). These were then sonicated using a Misonix immersed sonicator for 2 hours, which reduced the mean particle size to 150-200 nm. The resulting modified yellow pigment dispersions were diafiltered using a 50 nm diafiltration membrane column and concentrated to a solids content of 11-13%. These were then centrifuged at 5,000 rpm, and the solids level was adjusted to 10% by diafiltration. The final modified yellow pigment dispersions were found to be stable both at room temperature as well as at elevated temperatures (60-70° C.) for many weeks not only in an aqueous medium but also in the presence of 10% by weight organic solvents in the aqueous medium, such as isopropanol, N-methylpyrrolidone, and 2-pyrrolidone.

In addition, the sodium content of the dispersions of Examples 4-6 was determined by ion-selective electrode. Results are shown in Table 6 below.

TABLE 6

| Example No. | Pigment | $R^1$ | $R^2$ | $Na^+$ (ppm) |
| --- | --- | --- | --- | --- |
| Example 4 | Example 1 | H | F | 1500 |
| Example 5 | Example 2 | F | H | 2300 |
| Example 6 | Example 3 | H | F | 950 |

These results indicate that the dispersions comprising the modified yellow pigments of the present invention could be used in an inkjet ink composition.

Examples 7-9 and Comparative Example 13

Inkjet Ink Print Performance

Inkjet ink compositions of the present invention were prepared using the formulation shown in Table 7 below. The modified yellow pigments of Examples 4-6 were used as the pigment for the inkjet ink compositions of Example 7-9 respectively.

TABLE 7

| Ingredient | Amount |
|---|---|
| 2-pyrrolidinone | 7% |
| 1,5-pentanediol | 7% |
| trimethylolpropane | 5% |
| Surfynol 465 | 0.2% |
| pigment | 4% |
| water | 76.8% |

The resulting inkjet inks were printed using Canon I-550 printer on both plain paper (Xerox 4024 HP printing paper) and photo paper (Epson Premium Glossy Photopaper and HP Premium Plus Photopaper). Print performance results are summarized in Table 8 below. Also included are print performance results for a comparative inkjet ink composition using the same ink formulation except using a modified Pigment Yellow 74 which is an azo pigment having attached benzenesulfonic acid groups (Comparative Example 13). Print chroma and hue were measured using a Macbeth 7000A spectrocolorimeter with Xerox 4024 plain paper as a substrate.

TABLE 8

| Example No. | Pigment | $R^1$ | $R^2$ | $Na^+$ (ppm) | Chroma | Hue |
|---|---|---|---|---|---|---|
| Example 7 | Example 1 | H | F | 1,500 | 69.4 | 88.5 |
| Example 8 | Example 2 | F | H | 950 | 75.7 | 88.7 |
| Example 9 | Example 3 | H | F | 2,300 | 75.4 | 91.9 |
| Comp. Ex. 13 | mod PY74 | — | — | 2,500 | 61.7 | 97.8 |

As the results in Table 8 show, all images produced using the inkjet ink compositions of the present invention have excellent color saturation. While the inkjet ink compositions of Examples 8 and 9 (prepared using a modified pigment comprising a mono-fluoroquinolonoquinolone) were more chromatic than the inkjet ink composition of Example 7 (prepared using a modified pigment comprising a bis-fluoroquinolonoquinolone), each of the inkjet ink compositions of present invention produced images which exceeded those produced using the modified PY74 pigment in chroma. These images also have a more desirable neutral yellow shade with hue angle close to 90°.

The printed images were also tested for lightfastness, which was measured by exposing the images to QUV-351 lamps for up to 1,000 hours at 0.7 W/m² irradiation level. The inkjet ink compositions of the present invention were found to produce images with outstanding lightfastness, with measured delta E values of 2.5-3.5, depending on the initial density of the print. By comparison, images, produced using the comparative inkjet ink composition faded dramatically, indicating that the colorant was undergoing nearly complete decomposition.

Thus, the results show that fluoroquinolonoquinolones can be used to prepared modified yellow pigments of the present invention, and these pigments can be used to produce inkjet ink compositions with improved overall print performance.

The foregoing description of preferred embodiments of the present invention has been presented for the purposes of illustration and description. It is not intended to be exhaustive or to limit the invention to the precise form disclosed. Modifications and variations are possible in light of the above teachings, or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A modified yellow pigment comprising a yellow pigment having attached at least one organic group, wherein the yellow pigment has the structure:

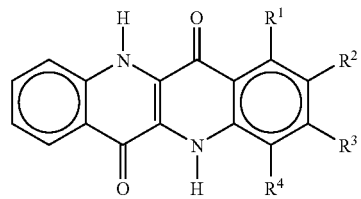

wherein $R^3$ is fluorine and $R^1$, $R^2$, and $R^4$ are hydrogen.

2. The modified yellow pigment of claim 1, wherein the organic group comprises at least one ionic group, at least one ionizable group, or mixtures thereof.

3. The modified yellow pigment of claim 1, wherein the organic group comprises at least one carboxylic acid group or salt thereof, at least one sulfonic acid group or salt thereof, at least one alkyl sulfate group, at least one alkyl amine group or salt thereof, or at least one alkyl ammonium group.

4. The modified yellow pigment of claim 1, wherein the organic group is a polymeric group.

5. An inkjet ink composition comprising a) a liquid vehicle and b) a modified yellow pigment comprising a yellow pigment having attached at least one organic group, wherein the yellow pigment has the structure:

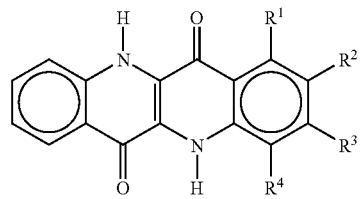

wherein $R^3$ is fluorine and $R^1$, $R^2$, and $R^4$ are hydrogen.

6. The inkjet ink composition of claim 5, wherein the organic group comprises at least one ionic group, at least one ionizable group, or mixtures thereof.

7. The inkjet ink composition of claim 5, wherein the organic group comprises at least one carboxylic acid group or salt thereof, at least one sulfonic acid group or salt thereof, at least one alkyl sulfate group, at least one alkyl amine group or salt thereof, or at least one alkyl ammonium group.

8. The inkjet ink composition of claim 5, wherein the organic group is a polymeric group.

9. The inkjet ink composition of claim 5, wherein the liquid vehicle is an aqueous vehicle.

10. The inkjet ink composition of claim 5, wherein the liquid vehicle is a non-aqueous vehicle.

11. An inkjet ink set comprising the inkjet ink composition of claim 5.

12. A composition comprising the modified yellow pigment of claim 1, wherein the composition is a plastic composition, an aqueous coating composition, a rubber composition, a paper composition, or a textile composition.

13. An aqueous composition comprising the modified yellow pigment of claim 1, wherein the aqueous composition is an automotive coating composition, an industrial coating composition, a paint composition, a toner composition, an adhesive composition, a latex composition, or an ink composition.

* * * * *